United States Patent
Chen et al.

(10) Patent No.: US 8,968,765 B2
(45) Date of Patent: Mar. 3, 2015

(54) BRUSH POLYMER AND MEDICAL USE THEREOF

(75) Inventors: Jui-Hsiang Chen, Hsinchu (TW); Jean-Dean Yang, Dayuan Township, Taoyuan County (TW); Yu-Hua Chen, Taichung (TW); Ting-Yu Shih, Taipei (TW); Chia-wei Hong, Taoyuan (TW); Chao-Chen Tien, Zhudong Township, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 50 days.

(21) Appl. No.: 13/595,561

(22) Filed: Aug. 27, 2012

(65) Prior Publication Data

US 2013/0149542 A1 Jun. 13, 2013

(30) Foreign Application Priority Data

Dec. 12, 2011 (TW) .............................. 100145724 A

(51) Int. Cl.
*C08L 101/08* (2006.01)
*C09D 175/04* (2006.01)
*A61L 15/22* (2006.01)

(52) U.S. Cl.
USPC ..... 424/426; 424/445; 428/423.3; 428/424.4; 428/424.6; 428/424.8; 523/105; 427/2.1; 427/2.24; 427/2.25; 623/1.46

(58) Field of Classification Search
USPC .................... 428/423.3, 424.4, 424.6, 424.8; 424/426, 445; 523/105; 427/2.1, 2.24, 427/2.25; 623/1.46
See application file for complete search history.

(56) References Cited

U.S. PATENT DOCUMENTS

| | | |
|---|---|---|
| 6,254,634 B1 | 7/2001 | Anderson et al. |
| 7,129,209 B2 | 10/2006 | Rhee |
| 7,173,102 B2 | 2/2007 | DeGrado et al. |
| 7,276,474 B2 | 10/2007 | Marchant et al. |
| 7,427,410 B2 | 9/2008 | Hubbell et al. |
| 7,629,029 B2 | 12/2009 | Mao et al. |
| 7,645,504 B1 | 1/2010 | Pacetti |

(Continued)

FOREIGN PATENT DOCUMENTS

| | | |
|---|---|---|
| CN | 101297982 A | 11/2008 |
| EP | 1987851 A2 | 11/2008 |

(Continued)

OTHER PUBLICATIONS

L.A. Dailey et al., "The role of branched polyesters and their modifications in the development of modern drug delivery vehicles," Journal of Controlled Release, Elsevier, vol. 101, No. 1-3, Jan. 3, 2005, pp. 137-149.

(Continued)

*Primary Examiner* — Thao T. Tran
(74) *Attorney, Agent, or Firm* — Muncy, Geissler, Olds & Lowe, P.C.

(57) ABSTRACT

The present disclosure provides a brush polymer, including: a linear polymer main chain; and brush structural side chains, including: a hydrophobic molecular branch, and a hydrophilic molecular branch and/or an anti-biofilm/or an antimicrobial molecular branch, wherein the linear polymer main chain is conjugated to the side chains by covalent bonds formed between a hydroxyl group and a reactive functional group, wherein the reactive functional group includes: isocyanate, carboxyl, or epoxy. The present disclosure also provides a medical application of the brush polymer.

17 Claims, 6 Drawing Sheets

(56) References Cited

U.S. PATENT DOCUMENTS

| | | | |
|---|---|---|---|
| 7,682,648 B1* | 3/2010 | Ding et al. | 427/2.24 |
| 7,795,326 B2 | 9/2010 | Salamone et al. | |
| 8,383,156 B2 | 2/2013 | Zhao | |
| 2007/0224236 A1* | 9/2007 | Boden | 424/423 |
| 2009/0155335 A1 | 6/2009 | O'Shaughnessey et al. | |
| 2009/0280157 A1* | 11/2009 | Maas et al. | 424/426 |

FOREIGN PATENT DOCUMENTS

| | | |
|---|---|---|
| WO | WO 99/52560 | 10/1999 |
| WO | WO 0067816 | 11/2000 |

OTHER PUBLICATIONS

Tan, et al., "Nonfouling biomaterials based on polyethylene oxide-containing amphiphilic triblock copolymers as surface modifying additives: Protein adsorption on PEO-copolymer/polyurethane blends", Wiley Periodicals, Inc., 2007, pp. 873-880.

Llanos, et al., "Immobilization of poly(ethylene glycol) onto a poly(vinyl alcohol) hydrogel: 2. Evaluation of thrombogenicity", Journal of Biomedical Materials Research, vol. 27, 1993, pp. 1383-1391.

Tan, et al., "Nonfouling Biomaterials Based on Polyethylene Oxide-Containing Amphiphilic Triblock Copolymers as Surface Modifying Additives: Synthesis and Characterization of Copolymers and Surface Properties of Copolymer-Polyurethane Blends", Wiley InterScience, 2008, pp. 1617-1628.

Ran, et al., "Biocompatibility of modified polyethersulfone membranes by blending an amphiphilic triblock co-polymer of poly(vinyl pyrrolidone)-b-poly(methyl methacrylate)-b-poly(vinyl pyrrolidone)", Acta Biomaterialia 7, 2011, pp. 3370-3381.

Dayananda, et al., "pH- and temperature-sensitive multiblock copolymer hydrogels composed of poly(ethylene glycol) and poly(amino urethane)", Polymer 49, 2008, pp. 4968-4973.

Lee, et al., "Platelet adhesion onto segmented polyurethane film surfaces modified by addition and crosslinking of PEO-containing block copolymers", Biomaterials 21, 2000, pp. 683-691.

Freij-Larsson, et al., "Polyurethane surfaces modified by amphiphilic polymers: effects on protein adsorption", Biomaterials 21, 2000, pp. 307-315.

Ikeda, et al., "Polyurethane elastomer with PEO-PTMO-PEO soft segment for sustained release of drugs", Biomaterials, vol. 11, 1990, pp. 553-559.

Bromberg, et al., "Self-Assembly in Aqueous Solutions of Poly(ethylene oxide)-b-poly(propylene oxide)-b-poly(ethylene oxide)-b-poly(vinyl alcohol)", Langmuir 15, 1999, pp. 8633-8639.

Rutnakornpituk, et al., "Synthesis, characterization and properties of chitosan modified with poly(ethylene glycol)-polydimethylsiloxane amphiphilic block copolymers", Polymer 46, 2005, pp. 9742-9752.

Chinese Office Action for Chinese Application No. 201110461181.4 dated Jun. 16, 2014.

* cited by examiner

BRUSH POLYMER AND MEDICAL USE THEREOF

CROSS REFERENCE TO RELATED APPLICATIONS

This application claims priority of Taiwan Patent Application No. 100145724, filed on Dec. 12, 2011, the entirety of which is incorporated by reference herein.

BACKGROUND OF THE DISCLOSURE

1. Technical Field

The present disclosure relates to a functional polymer and its applications in medical devices, and particularly relates to a brush polymer and its applications in medical wound dressings and medical catheters.

2. Description of the Related Art

When surfaces of most medical devices or biomedical materials contact with body fluid, such as exudates, urine, or blood . . . etc., nonspecific protein adsorption in the body fluid may occur. If such nonspecific protein adsorption occurs at the injured area, a large amount of proteins will accumulate to the surface of a medical device or a biomedical material, and begin to attract adjacent cells of tissue to migrate onto surface of medical devices during the tissue regeneration. Then, a large amount of cells will continuously accumulate in the spacing between the wound dressing matrix and dressing matrix to form an alternate construction. This phenomenon is called wound adhesion. When it occurs in a urinary system, the proteins or bacteria in urine may adhere to the surface of a medical device or a biomedical material, and then the bacteria will proliferate to form a biofilm, and it probably causes infection and blockage due to "encrustation" of the medical device, such as a catheter. When it occurs in a vascular system, the proteins or bacteria in blood may adhere to the surface of a medical device or a biomedical material, and then the nonspecific proteins will induce adhesion and activation of platelet in blood to form a thrombus.

Polyethylene glycol (PEG) is a well known hydrophilic material capable of inhibiting protein absorption and is typically chemically shifted onto a surface of a medical device or a biomedical material after the surface is activated by plasma, ozone, or corona. However, for a medical device or a biomedical material having an irregular shape, a considerable thickness, or a porous structure, a uniform hydrophilic interface and an optimized hydrophilic effect may not be obtained by such a method.

Accordingly, what is needed in the art is a multifunctional polymer material, capable of being formed into a uniformly hydrophilic surface and inhibiting nonspecific protein or bacteria adsorption.

BRIEF SUMMARY

The present disclosure provides a brush polymer, comprising: a linear polymer main chain; and brush structural side chains, comprising: a hydrophobic molecular branch, and a hydrophilic molecular branch and/or an anti-biofilm or an anti-microbial molecular branch, wherein the linear polymer main chain is conjugated to the brush structural side chains by covalent bonds formed between a hydroxyl group and a reactive functional group, wherein the reactive functional group comprises: isocyanate, carboxyl, or epoxy.

The present disclosure also provides a method for modifying a medical device, comprising: providing the above described brush polymer; dissolving the brush polymer in a solution; and coating or dipping a medical device with the solution containing the brush polymer followed by a drying process, such that the brush polymer is attached to a surface of the medical device.

The present disclosure further provides a medical device, wherein the medical device has the above described brush polymer adhered to its surface and/or mixed therein.

A detailed description is given in the following embodiments.

DETAILED DESCRIPTION

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative, and do not limit the scope of the disclosure.

Figure 1:
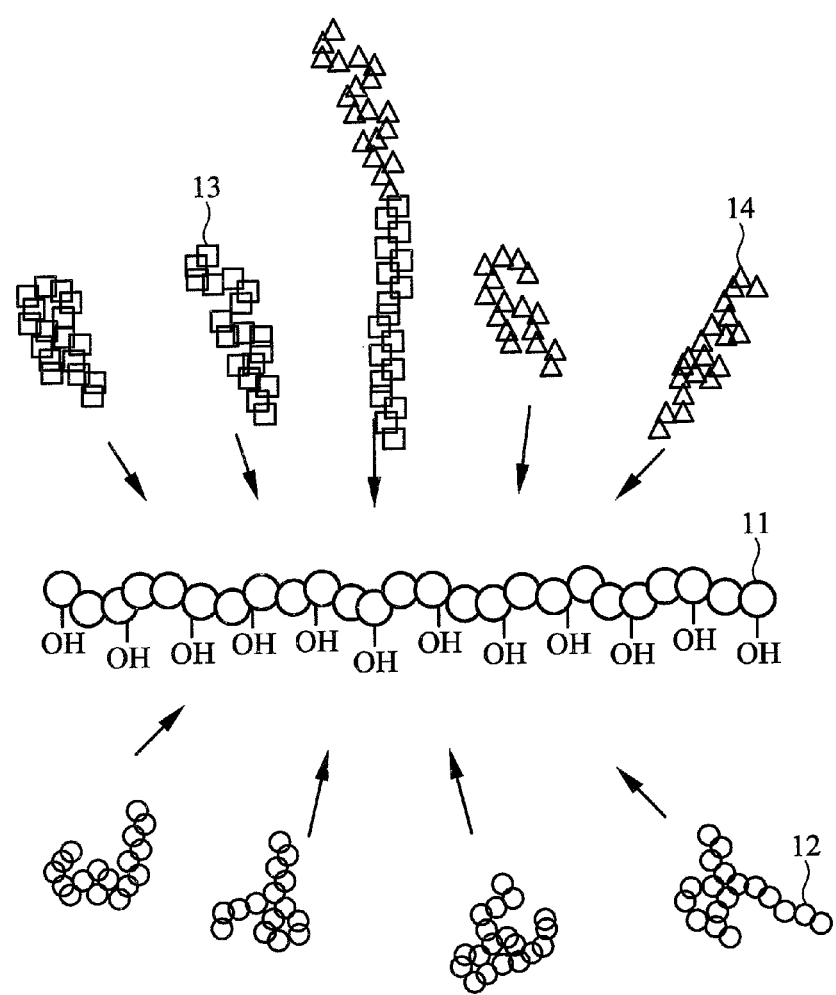
FIG. 1 is a schematic view illustrating the structure of a brush polymer according to an embodiment.

FIG. 1 illustrates the structure of the brush polymer according to an embodiment of the present disclosure. The brush polymer of the present disclosure generally includes: (a) a linear polymer main chain; and (b) brush structural side chains. The linear polymer main chain (a) is for example, a hydroxyl-containing linear main chain 11. The brush structural side chains (b) include: (b1) a hydrophobic molecular branch 12, and (b2) a hydrophilic molecular branch 13 and/or an anti-biofilm or an anti-microbial molecular branch 14. The linear polymer main chain is conjugated to the brush structural side chains by covalent bonds formed between a hydroxyl group and a reactive functional group, wherein the reactive functional group may include: isocyanate, carboxyl, or epoxy. In the brush polymer of the present disclosure, the hydrophobic molecular branch 12 may couple to a hydrophobic surface of a medical device by physical adhesion, and the hydrophilic molecular branch 13 may increase the hydrophilicity of surface of a medical device to decrease friction coefficient, inhibit protein adsorption, suppress attachment of cells of the living body, and prevent adhesion of the biological tissues. In addition, the anti-biofilm or the anti-microbial molecular branch 14 may have antimicrobial activity and suppress bacterial growth and biofilm formation. In an embodiment, the brush polymer may further contain a free hydroxyl group for further chemical modifications to improve the practical utility of the brush polymer for other surface modifications of medical devices.

Figure 2A:
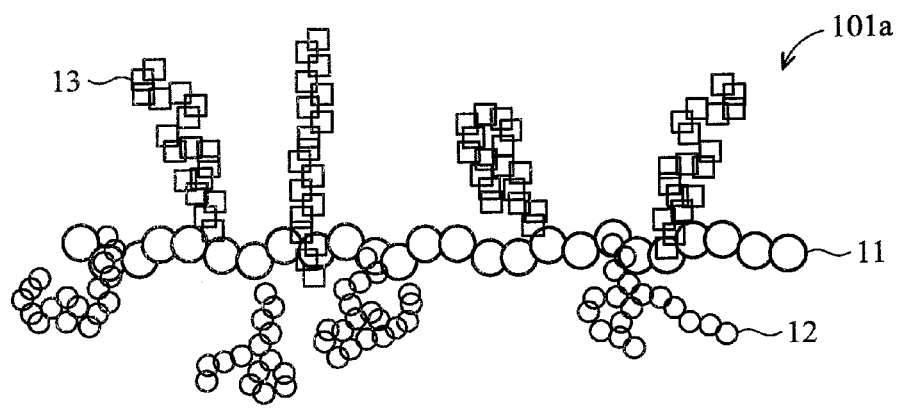
FIGS. 2a to 2e are schematic views illustrating structures of five brush polymers respectively according to alternative embodiments of the present disclosure.

FIG. 2a illustrates a schematic view of a structure of the brush polymer 101a according to an embodiment of the present disclosure, wherein the brush polymer comprises: a linear polymer main chain 11; and brush structural side chains comprising a hydrophobic molecular branch 12, and a hydrophilic molecular branch 13.

Figure 2B:
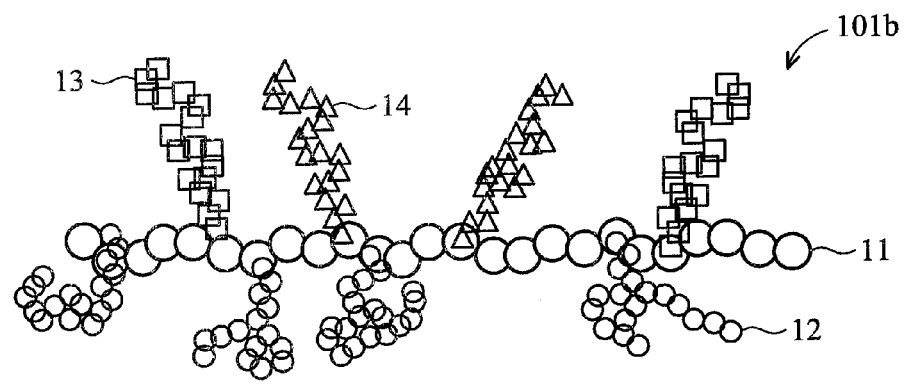

FIG. 2*b* illustrates a schematic view of a structure of the brush polymer 101*b* according to an embodiment of the present disclosure, wherein the brush polymer comprises: a linear polymer main chain 11; and brush structural side chains comprising a hydrophobic molecular branch 12, a hydrophilic molecular branch 13 and/or an anti-biofilm or an anti-microbial molecular branch 14.

Figure 2C:
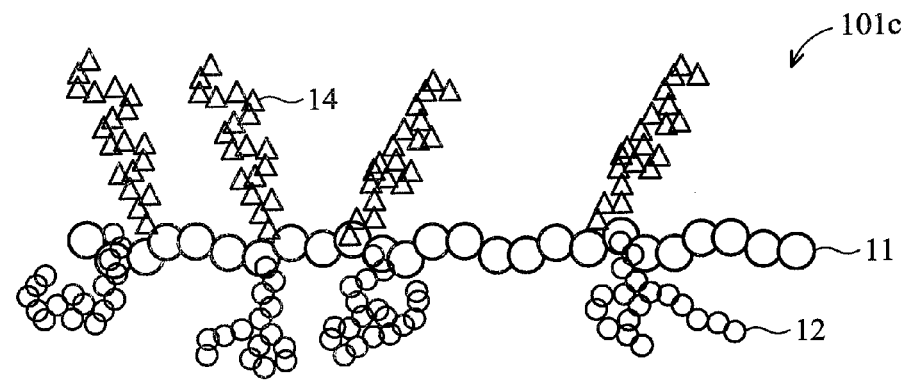

FIG. 2*c* illustrates a schematic view of a structure of the brush polymer 101*c* according to the embodiments of the present disclosure, wherein the brush polymer comprises: a linear polymer main chain 11; and brush structural side chains comprising a hydrophobic molecular branch 12 and/or an anti-biofilm or an anti-microbial molecular branch 14.

Figure 2D:
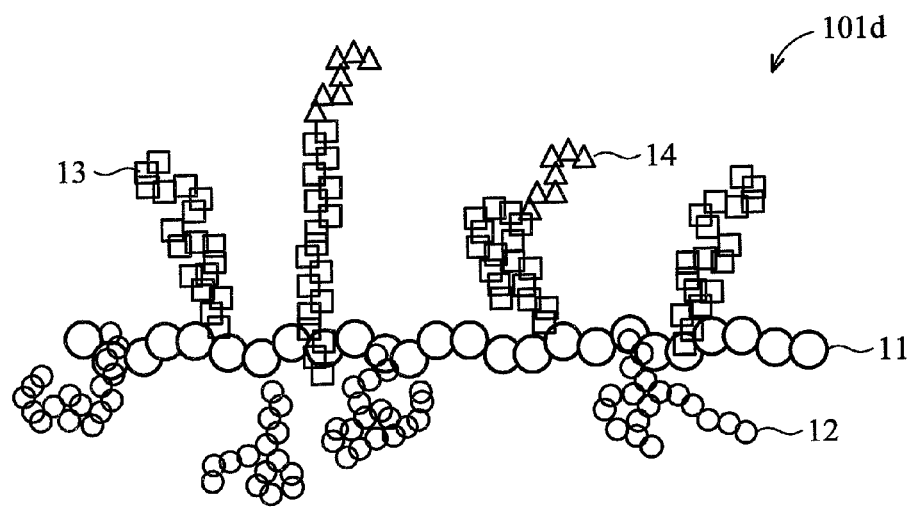
Figure 2E:
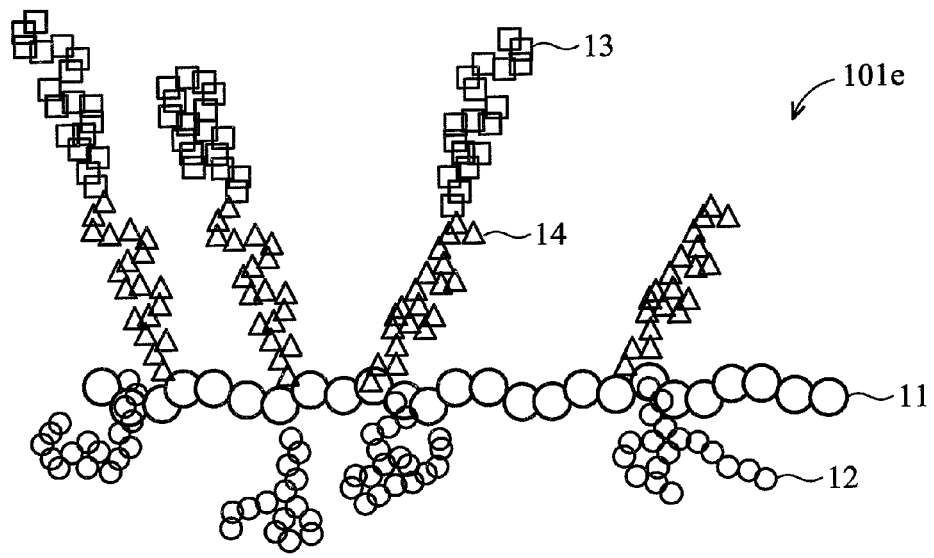

FIG. 2*d* illustrates a schematic view of a structure of the brush polymer 101*d* according to the embodiments of the present disclosure. The brush polymer comprises: a linear polymer main chain 11; and brush structural side chains comprising a hydrophobic molecular branch 12, a hydrophilic molecular branch 13 and/or an anti-biofilm or an anti-microbial molecular branch 14, wherein the anti-biofilm or the anti-microbial molecular branch 14 conjugates onto the hydrophilic molecular branch 13 by a covalent bond, and the hydrophilic molecular branch 13 conjugates onto the linear polymer main chain 11.

FIG. 2*d* illustrates a schematic view of a composition of the brush polymer 101*d* according to the embodiments of the present disclosure. The brush polymer comprises: a linear polymer main chain 11; and brush structural side chains comprising a hydrophobic molecular branch 12, a hydrophilic molecular branch 13 and/or an anti-biofilm or an anti-microbial molecular branch 14, wherein the hydrophilic molecular branch 13 conjugates onto the anti-biofilm or the anti-microbial molecular branch 14 by a covalent bond, and the anti-biofilm or the anti-microbial molecular branch 14 conjugates onto the linear polymer main chain 11.

In the brush polymer of the present disclosure, the linear polymer main chain containing a hydroxyl group may be selected from a linear or a branched polymer which is either synthetic or natural, preferably a linear synthetic polymer. The linear synthetic polymer may include, but is not limited to: polyvinyl alcohol (PVA), polyvinyl acetate (PVAc), poly (vinyl alcohol-co-vinyl acetate), poly(ethylene vinyl-co-alcohol) (EVOH), polysaccharide, or combinations thereof. The natural polymer may be a polysaccharide including, but not limited to: hyaluronic acid, cellulose, dextran, chitin, chitosan, alginate, carrageenan, starch, pectin, gum Arabic, guar gum, pullulan, scleroglucan, gellan, chondroitin sulfate, heparin, keratin sulfate, derivatives thereof, or combinations thereof. The linear polymer main chain has a weight-average molecular weight of about 500 to 2000,000 dalton, preferably 5,000 to 1000,000.

In the brush polymer of the present disclosure, the hydrophobic molecular branch includes, but is not limited to: a polymer segment containing urethane repeating units, a polymer segment containing polypropylene oxide (PPO) repeating units, a polymer segment containing ethylene repeating units, a polymer segment containing propylene repeating units, a polymer segment containing styrene repeating units, a polymer segment containing sulfone repeating units, or combinations thereof, wherein the polymer segment containing urethane repeating units comprises: aliphatic polyurethane, aromatic polyurethane, or combinations thereof. The hydrophobic molecular branch has a weight-average molecular weight of about 500 to 50,000 dalton.

In the brush polymer of the present disclosure, the hydrophilic molecular branch includes, but is not limited to: polyethylene glycol (PEG), polyethylene oxide (PEO), polyvinylpyrrolidone (PVP), polyacrylic acid (PAA), polymethacrylic acid (PMA), or combinations thereof, preferably including: polyethylene glycol, (PEG), polyethylene oxide (PEO), polyvinylpyrrolidone (PVP), or combinations thereof, wherein the hydrophilic molecular branch has a weight-average molecular weight of about 500 to 100,000 dalton, preferably about 500 to 50,000 dalton, and more preferably about 500 to 30,000 dalton.

In the brush polymer according to another embodiment, an anti-biofilm or an anti-microbial molecular branch may further be conjugated thereto by chemical bonding or physical adhesion, wherein the anti-biofilm or the anti-microbial molecular branch includes, but is not limited to: farnesol, xylitol, lactoferrin, ethylene diamine tetraacetic acid (EDTA), gallium, PNAG-degrading enzyme, RNA-III inhibiting peptide, furanone C30, silver, iodine, zinc, copper, an antibiotic, medicine or combinations thereof, preferably includes farnesol or xylitol, and more preferably includes farnesol.

The anti-biofilm or the anti-microbial molecular branch may be conjugated directly onto the linear polymer main chain by chemical bonding or physical adhesion, or be conjugated onto the hydrophilic molecular branch or the hydrophobic molecular branch by chemical bonding or physical adhesion.

The hydrophobic molecular branch, the hydrophilic molecular branch, or an anti-biofilm or an anti-microbial molecular branch may be conjugated to the linear polymer main chain by a covalent bond to form the brush polymer through a reaction between its intrinsic or modified functional group (such as isocyanate, carboxyl, or epoxy) with main chain's functional group (such as hydroxyl). For example, when the linear polymer main chain has a hydroxyl (—OH) group and the brush structural side chain polymer has an isocyanate (—NCO) group, the covalent bond formed therebetween is a urethane linkage (—O(C═O)NH—); and when the linear polymer main chain has a hydroxyl (—OH) group and the brush structural side chain polymer has a carboxyl (—COOH) group, the covalent bond formed therebetween is an ester linkage; when the linear polymer main chain has a hydroxyl (—OH) group and the brush structural side chain polymer has an epoxy group, the covalent bond formed therebetween is an ether linkage.

Figure 3:
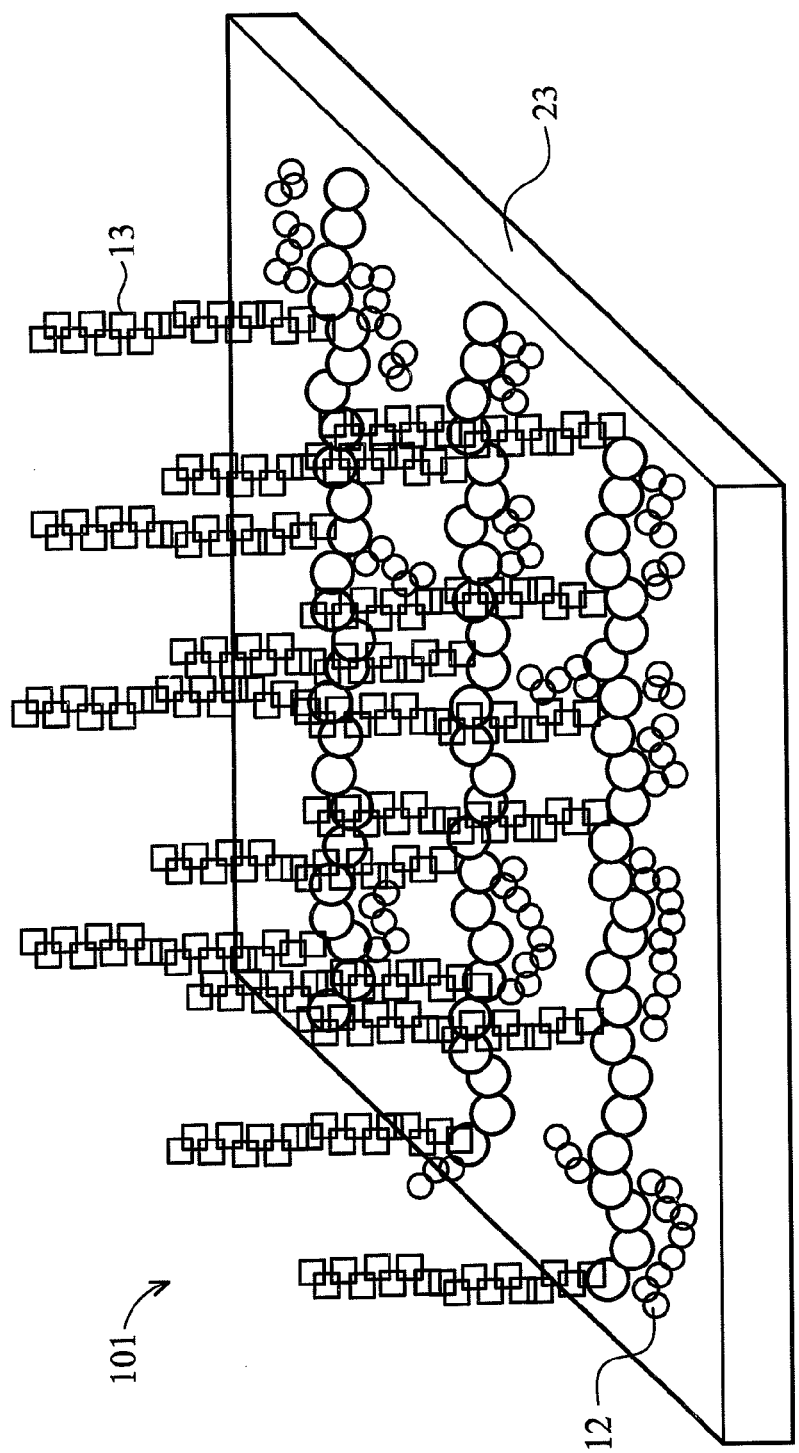
FIG. 3 illustrates a schematic view of a medical device with its surface modified by a brush polymer according to embodiments of the present disclosure.

Referring to FIG. 3, the present disclosure also provides a method for modifying a surface 23 of a medical device, including: providing a brush polymer 101; dissolving the brush polymer 101 in a solution; and coating or dipping a medical device with the solution containing the brush polymer 101 followed by a drying process, such that the brush polymer 101 is attached to a surface 23 of the medical device to achieve surface modification. As shown in FIG. 3, the hydrophobic molecular branch 12 of the brush polymer 101 is attached to the hydrophobic surface 23 of the medical device by physical adhesion, while the hydrophilic molecular branch is arranged in a brush structure. The solution for dissolving the brush polymer includes, but is not limited to: N,N-dimethylformamide (DMF), N,N-dimethylacetamide (DMAc), dimethyl sulfoxid (DMSO), tetrahydrofuran (THF), alcohols, ketones, water, or combinations thereof. Preferable solutions includes: N,N-dimethylacetamide (DMAc), ketones, water, or combinations thereof. More preferable solutions includes the following combinations: (a) butanone and water, (b) acetone and N,N-dimethylacetamide (DMAc), (c) acetone, water, and N,N-dimethylacetamide (DMAc), or (d) acetone, N,N-dimethylacetamide (DMAc), and dimethyl sulfoxid (DMSO).

In an embodiment, the solid content of the brush polymer dissolved in the solution is between 0.01 wt % and 50 wt %, preferably between 0.1 wt % and 30 w % t, more preferably between 0.1 wt % and 20 wt %.

In an embodiment, a medical device is coated or dipped with the solution containing the brush polymer followed by a drying process, such as by hot air or under vacuum, at a temperature of room temperature to 200° C., preferably 30° C. to 100° C.

In addition to the surface modification by coating or dipping the medical device with the solution containing the brush polymer, the brush polymer may be blended with the polymer of the medical device. The method for blending the brush polymer with the polymer may include, but is not limited to: melt blending or solvent blending. The polymer includes, but is not limited to: thermoplastic polyurethane (TPU), polyurethane (PU), polyvinyl alcohol (PVA), polyethylene (PE), polypropylene (PP), polyvinyl chloride (PVC), polystyrene, polyvinyl acetate (PVAc), poly(vinyl alcohol-co-vinyl acetate, poly(ethylene vinyl-co-alcohol) (EVOH), polysulfone, poly ether sulfone, derivatives thereof or combinations thereof.

Therefore, the brush polymer may be dissolved in the solution to physically adhere to a hydrophobic material or a surface of a medical device; or it may be distributed in a hydrophobic material or an interior and an outer surface of a medical device by blending. As the hydrophilic molecular branches of the brush polymer are exposed to the surface of medical device, the hydrophilic molecular branches may form a steric hindrance on the surface, and arrange into a cilia structure due to entropic repulsion to expel the approaching protein molecules, thereby inhibiting the protein adsorption with the substrate, as well as promoting the hydrophilicity of a modified surface of a medical device to decrease friction coefficient, suppressing attachment of cells of the living body, preventing adhesion of the biological tissues, and inhibiting microbial adhesion. Furthermore, the anti-biofilm or the anti-microbial molecular branch may be conjugated to the side chain of the brush polymer by a covalent bond, such that the modified surface of the medical device or the biomedical material have antimicrobial activity and an ability to suppress bacterial growth and biofilm formation.

In summary, the brush polymer may be distributed in a hydrophobic material or an interior and an outer surface of a medical device by physical adhesion or blending. The medical device may include, but is not limited to: a wound dressing, a catheter, a vascular access device, a hemodialyzer, a stent, a biliary stent, or an implantable device.

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative, and do not limit the scope of the disclosure.

EXAMPLE 1

Hydrophobic Molecular Branch Prepolymer (A) (mPU$_{(BDO)}$-NCO)

The hydrophobic molecular branch prepolymer (A) was prepared as follows: 1.53 g of 1,4-butanediol (1,4-BDO) was placed in a round-bottom flask. 7.65 ml of an N,N-dimethylacetamide (DMAc) solvent was added thereto and slowly heated to a temperature of 60° C. followed by thorough mixing. Then 8.42 g of diphenylmethane-4,4'-diisocyanate (MDI) was dissolved in 42.35 ml of N,N-dimethylacetamide (DMAc) and the solution was dripped slowly into the flask under nitrogen at a temperature of 50° C. for 3 hours. Thereafter, a sample of the reaction mixture was subjected to molecular weight analysis. The weight-average molecular weight measured by gel permeation chromatography (GPC) was about 2,243 dalton. Then, 0.12 ml of methanol diluted with 0.6 ml of DNAc was dripped slowly into the flask to form a hydrophobic prepolymer with single side activity.

EXAMPLE 2

Hydrophobic Molecular Branch Prepolymer (B) (mC$_8$PU$_{8,000}$-NCO)

The hydrophobic molecular branch prepolymer (B) was prepared as follows: 19.5 g of PolyTetramethylene-ether-Glycol (PTMEG1000) and 36 ml of N,N-dimethylacetamide (DMAc) were placed in a 150 ml two-neck flask. 2.325 g of diphenylmethane-4,4'-diisocyanate (MDI) was added into 4 ml of DMAc using an isobaric funnel. The mixture was uniformly mixed and heated to a temperature of 65° C. for reaction for 2 hours to obtain the prepolymer. The prepolymer was cooled to room temperature and C$_8$-NCO and a catalyst were added into the prepolymer, uniformly mixed and heated followed by heating to a temperature of 65° C. for reaction for 2 hours to obtain a mC$_8$-prepolymer.

Then, 2.325 g of MDI in 4 ml of DMAc was added slowly into the mC$_8$-prepolymer, mixed uniformly and heated to a temperature of 60° C. for reaction for 3 hours to obtain the mC$_8$PU hydrophobic molecular branch prepolymer (B). The weight-average molecular weight of the mC$_8$PU hydrophobic molecular branch prepolymer (B) measured by gel permeation chromatography (GPC) was about 8,000 dalton.

EXAMPLE 3

Hydrophobic Molecular Branch Prepolymer (C) (mPPO$_{2,500}$-NCO)

2.9 g of modified polyphenylene oxide (mPPO, weight-average molecular weight of 2,500) was dissolved in 4 ml of N,N-dimethylacetamide (DMAc), and then 0.275 g of diphenylmethane-4,4'-diisocyanate (MDI) and 2 ml of DMAc were added into a 25 ml two-neck flask and dissolved. The modified polyphenylene oxide (mPPO, weight-average molecular weight of 2,500) was added slowly into the MDI solution, mixed uniformly, and the mixture was heated to a temperature of 60° C. for reaction for 2 hours, to obtain mPPO$_{2500}$-NCO.

EXAMPLE 4

Hydrophobic Molecular Branch Prepolymer (D) (mPPU$_{4,923}$-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day in advance. The hydrophobic molecular branch prepolymer (D) was prepared as follows: 5.32 g of diphenylmethane-4,4'-diisocyanate (MDI) and 26.6 ml of DMAc were added into a 250 ml two-neck flask and stirred to dissolve at room temperature. 0.58 g of 1,4-butanediol (BDO) was added into 2.9 ml of DMAc with thorough mixing. The mixture of 1,4-butanediol (BDO) and DMAc was added into the MDI solution, and uniformly mixed and heated to a temperature of between 60±5° C. for reaction for 3 hours to obtain a prepolymer. The weight-average molecular weight of the prepolymer measured by gel permeation chromatography (GPC) was about 1,447 dalton.

10.3 g of modified polyphenylene oxide (mPPO, weight-average molecular weight of 2,500) and 51.5 ml of DMAc were added into a 150 ml single-neck flask and shaken to dissolve at room temperature. The mPPO solution was placed in an isobaric funnel and dripped slowly into the 60±5° C. prepolymer solution for about 30 minutes. After the addition of the mPPO solution was completed, the solution was stirred at 60±5° C. for 2.5 hours to obtain $mPPO_{2,500}$-b-$PU_{1,447}$-NCO (mPPU-NCO) prepolymer. The weight-average molecular weight of the $mPPO_{2,500}$-b-$PU_{1,447}$-NCO (mPPU-NCO) prepolymer measured by gel permeation chromatography (GPC) was about 4,923 dalton ($mPPU_{4,923}$-NCO).

EXAMPLE 5

Hydrophobic Molecular Branch Prepolymer (E) ($mPPU_{9,764}$-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day in advance. The hydrophobic molecular branch prepolymer (E) was prepared as follows: 25.16 g of diphenylmethane-4,4'-diisocyanate (MDI) and 126 ml of DMAc were added into a 250 ml two-neck flask and stirred to dissolve at room temperature. 5.44 g of 1,4-butanediol (BDO) was added into 27 ml of DMAc with thorough mixing. The mixture of 1,4-butanediol (BDO) and DMAc was added into the MDI solution, and uniformly mixed and heated to a temperature of between 60±5° C. for reaction for 3 hours to obtain a prepolymer. The weight-average molecular weight of the prepolymer measured by gel permeation chromatography (GPC) was about 4,581 dalton.

10.22 g of modified polyphenylene oxide (mPPO, weight-average molecular weight of 2,500) and 51.5 ml of DMAc were added into a 150 ml single-neck flask and shaken to dissolve at room temperature. The mPPO solution was placed in an isobaric funnel and dripped slowly into the 60±5° C. prepolymer solution for about 30 minutes. After the addition of the mPPO solution was completed, the solution was stirred at 60±5° C. for reaction for 2.5 hours to obtain $mPPO_{2,500}$-b-$PU_{4,581}$-NCO (mPPU-NCO) prepolymer. The weight-average molecular weight of $mPPO_{2,500}$-b-$PU_{4,581}$-NCO (mPPU-NCO) prepolymer measured by gel permeation chromatography (GPC) was about 9,764 dalton ($mPPU_{9,764}$-NCO).

EXAMPLE 6

Hydrophilic Molecular Branch Prepolymer ($mPEG_{5,000}$-NCO)

Before preparing the hydrophilic molecular branch prepolymer, N,N-dimethylacetamide (DMAc) solvent was dehydrated by a molecular sieve for one day and modified PEG (mPEG, weight-average molecular weight of 5000) was subjected to vacuum drying for 24 hours in advance. 80 g of $mPEG_{5000}$ and 120 ml N,N-dimethylacetamide (DMAc) solvent were added in a 500 ml two-neck flask and preheated to 60° C. for dissolution. Then, 3.5 g of diphenylmethane-4,4'-diisocyanate (MDI) was dissolved in 35 ml of DMAc, cooled to 40° C., and slowly added to the $mPEG_{5000}$ solution with thorough mixing. Thereafter, the solution was slowly heated to a temperature of 60° C. for reaction for 2 hours to obtain the hydrophilic $mPEG_{5000}$-NCO prepolymer.

EXAMPLE 7

Anti-Microbial Molecular Branch Prepolymer (A) (Farnesol-HDI-NCO)

Before preparing the anti-microbial molecular branch prepolymer, N,N-dimethylacetamide (DMAc) solvent was dehydrated by a molecular sieve for one day and 3,7,11-Trimethyl-2,6,10-dodecatrien-1-ol (Farnesol) was subjected to vacuum drying for 24 hours in advance. 5.818 g of Farnesol and 80 ml N,N-dimethylacetamide (DMAc) solvent were added in a 250 ml two-neck flask and stirred for dissolution. Then, 0.04 g of 1,4-diazabicyclo-(2,2,2) octane (DABCO) and 0.02 g of $Sn(Oct)_2$ (stannous octoate, Sn(II)) were dissolved in the Farnesol solution. After 4.182 g of 1,6-diisocyanatohexane (MI) was added slowly into 20 ml of DMAc and stirred for dissolution, the HDI solution was added slowly into the Farnesol solution with thorough mixing and heated to a temperature of 55-60° C. for reaction for 3 hours to obtain the anti-microbial molecular branch Farnesol-HDI-NCO prepolymer.

EXAMPLE 8

Anti-Microbial Molecular Branch Prepolymer (B) (Farnesol-IPDI-NCO)

Before preparing the anti-microbial molecular branch prepolymer, N,N-dimethylacetamide (DMAc) solvent was dehydrated by a molecular sieve for one day in advance. 0.72 g of Farnesol and 14 ml of N,N-dimethylacetamide (DMAc) solvent were added in a 500 ml two-neck flask and stirred for dissolution. Then, 0.1 g of 1,4-diazabicyclo-(2,2,2) octane (DABCO) and 0.05 g of $Sn(Oct)_2$ (stannous octoate, Sn(II)) were added slowly into 2 ml of DMAc in a 20 ml flask, and ultrasonicated for 30 minutes for dissolution. Then 0.056 ml of the above obtained solution was added into a 500 ml two-neck flask with thorough mixing and heated to a temperature of 55° C. for reaction for 3 hours to obtain the anti-microbial molecular branch prepolymer (B), Farnesol-IPDI-NCO.

EXAMPLE 9

Anti-Microbial Molecular Branch Prepolymer (C) (Farnesol-b-$PEG_{10,000}$-NCO)

Before preparing the anti-microbial molecular branch prepolymer, N,N-dimethylacetamide (DMAc) solvent and PEG diol (weight-average molecular weight of 10,000) were vacuum dried for 24 hours in advance. 30.76 g of PEG $diol_{10,000}$ and 307.6 ml of DMAc were added into a 500 ml two-neck flask and dissolved. The anti-microbial molecular branch prepolymer (B), Farnesol-IPDI-NCO obtained from Example 8 was then added into the 500 ml two-neck flask with thorough mixing and heated to a temperature of 65° C. for reaction for 16 hours to obtain the hydrophilic anti-microbial molecular branch prepolymer, Farnesol-b-$PEG_{10,000}$-NCO.

EXAMPLE 10

Anti-Microbial Molecular Branch Prepolymer (D) (Farnesol-b-PEG$_{2,000}$-NCO)

Before preparing the anti-microbial molecular branch prepolymer, N,N-dimethylacetamide (DMAc) solvent and PEG diol (weight-average molecular weight of 2,000) were vacuum dried for 24 hours in advance. 15.47 g of PEG diol$_{10,000}$ and 154.7 ml of DMAc were added into a 250 ml two-neck flask and dissolved. The anti-microbial molecular branch prepolymer (B), Farnesol-IPDI-NCO obtained from Example 8 is then added into the 500 ml two-neck flask with thorough mixing and heated to a temperature of 65° C. for reaction for 16 hours to obtain the hydrophilic anti-microbial molecular branch prepolymer, Farnesol-b-PEG$_{2,000}$-NCO.

EXAMPLE 11

Brush Polymer (A) (PVA$_{10,000}$-g-($_{60\%}$PEG$_{5,000}$-co-$_{30\%}$mC$_8$PU))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$.

56 ml of hydrophobic molecular branch prepolymer (B) (mC8PU8,000-NCO) of Example 2 was added to the above mentioned PVA$_{10,000}$-g-mPEG$_{5,000}$ product to obtain PVA$_{10,000}$-g-(60% PEG$_{5,000}$-co-30% mC$_8$PU). The graft ratio (moles of single bond/total moles of hydroxyl) of hydrophilic PEG molecular branch was 60%, and that of the hydrophobic molecular branch (mC$_8$PU) was 30%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 12

Brush Polymer (B) (PVA$_{10,000}$-g-($_{60\%}$PEG$_{5,000}$-co-$_{10\%}$mC$_8$PU))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$.

56 ml of hydrophobic molecular branch prepolymer (B) (mC$_8$PU$_{8,000}$-NCO) of Example 2 was added to the above mentioned PVA$_{10,000}$-g-mPEG$_{5,000}$ product, and the mixture was heated to a temperature of 60° C. for carrying out a reaction for 3 hours to obtain PVA$_{10,000}$-g-($_{60\%}$PEG$_{5,000}$-co-$_{10\%}$mC$_8$PU). The graft ratio of the hydrophilic PEG molecular branch was 60%, and that of the hydrophobic molecular branch (mC$_8$PU) was 10%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 13

Brush Polymer (C) (PVA$_{10,000}$-g-($_{30\%}$PEG$_{5,000}$-co-$_{10\%}$mC$_8$PU))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$.

56 ml of hydrophobic molecular branch prepolymer (B) (mC$_8$PU$_{8,000}$-NCO) of Example 2 was added to the above mentioned PVA$_{10,000}$-g-mPEG$_{5,000}$ product, and the mixture was heated to a temperature of 60° C. for carrying out a reaction for 3 hours to obtain PVA$_{10,000}$-g-($_{30\%}$PEG$_{5,000}$-co-$_{10\%}$mC$_8$PU). The graft ratio of the hydrophilic PEG molecular branch was 30%, and that of the hydrophobic molecular branch (mC$_8$PU) was 10%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 14

Brush Polymer (D) (PVA10,000-g-(60% PEG5,000-co-10% mC8PU))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$.

56 ml of hydrophobic molecular branch prepolymer (B) (mC$_8$PU$_{8,000}$-NCO) of Example 2 was added to the above mentioned PVA$_{10,000}$-g-mPEG$_{5,000}$ product, and the mixture was heated to a temperature of 60° C. for carrying out a reaction for 3 hours to obtain PVA$_{10,000}$-g-($_{60\%}$PEG$_{5,000}$-co-$_{10\%}$mC$_8$PU). The graft ratio of the hydrophilic PEG molecular branch was 60%, and that of the hydrophobic molecular branch (mC$_8$PU) was 10%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 15

Brush Polymer (E) (PVA$_{10,000}$-g-($_{90\%}$ PEG$_{5,000}$-co-$_{10\%}$ mC$_8$PU))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$.

56 ml of hydrophobic molecular branch prepolymer (B) (mC$_8$PU$_{8,000}$-NCO) of Example 2 was added to the above mentioned PVA$_{10,000}$-g-mPEG$_{5,000}$ product, and the mixture was heated to a temperature of 60° C. for carrying out a reaction for 3 hours to obtain PVA$_{10,000}$-g-($_{90\%}$ PEG$_{5,000}$-co-$_{10\%}$ PU). The graft ratio of the hydrophilic PEG molecular branch was 90%, and that of the hydrophobic molecular branch (mC$_8$PU) was 10%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 16

Brush Polymer (F) (PVA$_{10,000}$-g-($_{30\%}$ PEG$_{5,000}$-co-$_{10\%}$ PPO))

1 g of polyvinyl alcohol (PVA, weight-average molecular weight of 10,000) and 19 ml of N,N-dimethylacetamide (DMAc) solvent were added into a 50 ml two-neck flask and slowly heated to a temperature of 60° C. for dissolution, and then the above mentioned PVA$_{10,000}$ solution was cooled to room temperature, followed by addition of the mPEG$_{5,000}$-NCO prepolymer of Example 5. After mixing uniformly, the mixture was heated to a temperature of between 60±5° C. for reaction for 3 hours to obtain the product, PVA$_{10,000}$-g-PEG$_{5,000}$. 56 ml of hydrophobic molecular branch prepolymer (C) (mPPO$_{2500}$-NCO) of Example 3 was added to the above mentioned PVA$_{10,000}$-g-PEG$_{5,000}$ product to obtain PVA$_{10,000}$-g-($_{30\%}$ PEG$_{5,000}$-co-$_{10\%}$ PPO). The graft ratio of the hydrophilic PEG molecular branch was 60%, and that of the hydrophobic molecular branch (mPPO) was 10%.

The brush polymer was purified by a process as follows: the reacted product was dialysed in N,N-dimethylacetamide (DMAc) solution by MWCO:12K-14K dialysis membrane for 2 days, then dialysed in dimethyl sulfoxide (DMSO) solution by MWCO:12K-14K dialysis membrane for 2 days, and finally dialysed in water by MWCO:12K-14K dialysis membrane for 2 day and then freeze dried.

EXAMPLE 17

Brush Polymer (G) (PVA$_{10,000}$-g-(PEG$_{5,000}$-co-PPU$_{4,923}$))

Step 1. Hydrophilic Molecular Branch Prepolymer (mPEG$_{5,000}$-NCO)

Before preparing the hydrophilic molecular branch prepolymer, N,N-dimethylacetamide (DMAc) solvent was dehydrated by a molecular sieve for one day in advance and modified PEG (mPEG, weight-average molecular weight of 5000) was subjected to vacuum drying for 24 hours. 86.12 g of mPEG$_{5000}$ and 856 ml of N,N-dimethylacetamide (DMAc) solvent were added in a 1000 ml two-neck flask and preheated to 60° C. for dissolution. Then, 1.18 g, 1.37 g, and 1.54 g of diphenylmethane-4,4'-diisocyanate (MDI) were dissolved in 13 ml, 14 ml, and 18 ml of DMAc respectively in a 1000 ml two-neck flask and stirred at room temperature for dissolution. Then, the obtained solutions were heated to a temperature of between 60±5° C., while 320 ml, 286 ml, and 250 ml of mPEG$_{5000}$ solution were respectively placed in isobaric funnels and dripped slowly into diphenylmethane-4,4'-diisocyanate (MDI) solution in 2 hours. After the addition of the mPEG5000 solution was completed, the mixture was reacted at a temperature of 65° C. for 1 hour to obtain the hydrophilic mPEG$_{5000}$-NCO prepolymer.

Step 2. Hydrophobic Molecular Branch Prepolymer (PPO-b-PU-NCO, PPU-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day in advance. The prepolymer was prepared as follows: 5.32 g of diphenylmethane-4,4'-diisocyanate (MDI) and 26.6 ml of DMAc were added into a 250 ml two-neck flask and stirred to dissolve at room temperature. 0.58 g of 1,4-butanediol (BDO) was added into 2.9 ml of DMAc with thorough mixing. The mixture of 1,4-butanediol (BDO) and DMAc was added into the MDI solution with thorough mixing. Thereafter, the solution was heated to a temperature of between 60±5° C. for reaction for 3 hours to obtain a prepolymer. The weight-average molecular weight of the prepolymer measured by gel permeation chromatography (GPC) was about 1,447 dalton.

10.3 g of modified polyphenylene oxide (mPPO, weight-average molecular weight of 2,500) and 51.5 ml of DMAc were added into a 150 ml single-neck flask and shaken to dissolve at room temperature. The mPPO solution was placed in an isobaric funnel and dripped slowly into the 60±5° C. prepolymer solution in 30 minutes. After the addition of the mPPO solution was completed, the solution was stirred at 60±5° C. for 2.5 hours to obtain the PPU-NCO prepolymer. The weight-average molecular weight of the PPU-NCO prepolymer measured by gel permeation chromatography (GPC) was about 4,923 dalton.

Step 3. Brush Polymer

An amount of 1 g polyvinyl alcohol (PVA, weight-average molecular weight of 10,000) was added into 3 sample bottles each containing 6 mL of N,N-dimethylacetamide (DMAc), respectively, and the sample bottles were then placed in a drying oven at 65° C. for dissolution, and cooled to room temperature. Then, the obtained solution was respectively added 338 ml, 300 ml, and 263 ml of the above mentioned hydrophilic molecular branch prepolymer, mPEG$_{5000}$-NCO, and the mixture was heated to a temperature of between 60±5° C. for reaction for 3 hours to obtain the product, PVA$_{10,000}$-g-PEG$_{5,000}$. Then, 13.5 ml, 27 ml, and 40.5 ml of hydrophobic molecular branch prepolymer, mPPO$_{2500}$-

NCO, were respectively added into the above mentioned $PVA_{10,000}$-g-$PEG_{5,000}$ product, and 0.054 g, 0.01 g, and 0.0016 g of 1,4-diazabicyclo-(2,2,2) octane (DABCO) and 0.027 g, 0.0054 g, and 0.0008 g of $Sn(Oct)_2$ were respectively added with thorough mixing. Thereafter, the solution was heated to 65° C. for reaction for 16 hours to obtain $PVA_{10,000}$-g-($PEG_{5,000}$-co-PPU). The graft ratios of the hydrophilic PEG molecular branch were 70%, 80%, and 90% respectively, and that of the hydrophobic molecular branch (mPPU) were 30%, 20%, and 10% respectively.

The brush polymer was purified by a process as follows: the reacted product was dialysed in a dimethyl sulfoxide (DMSO) solution by MWCO: 25K dialysis membrane for 2 days, and finally dialysed in deionized water (DI water) by MWCO: 25K dialysis membrane for 2 day and then freeze dried.

EXAMPLE 18

Brush Polymer (H) (PVA-g-($PEG_{5,000}$-co-$PPU_{9,764}$))

Step 1. Hydrophilic Molecular Branch Prepolymer ($mPEG_{5,000}$-NCO)

Before preparing the hydrophilic molecular branch prepolymer, N,N-dimethylacetamide (DMAc) solvent was dehydrated by a molecular sieve for one day in advance, and modified PEG (mPEG, weight-average molecular weight of 5000) was subjected to vacuum drying for 24 hours. 86.12 g of $mPEG_{5000}$ and 856 ml of N,N-dimethylacetamide (DMAc) solvent were added in a 1000 ml two-neck flask and preheated to 60° C. for dissolution. Then, 1.18 g, 1.37 g, and 1.54 g of diphenylmethane-4,4'-diisocyanate (MDI) were dissolved in 13 ml, 14 ml, and 18 ml of DMAc respectively in a 1000 ml two-neck flask and stirred at room temperature for dissolution. Then, the obtained solutions were heated to a temperature of between 60±5° C., while 320 ml, 286 ml, and 250 ml of $mPEG_{5000}$ solution were respectively placed in isobaric funnels and dripped slowly into diphenylmethane-4,4'-diisocyanate (MDI) solution in 2 hours. After the addition of the $mPEG_{5000}$ solution was completed, the mixture was reacted at a temperature of 65° C. for 1 hour to obtain the hydrophilic $mPEG_{5000}$-NCO prepolymer.

Step 2. Hydrophobic Molecular Branch Prepolymer (PPO-b-PU-NCO, PPU-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day in advance. The prepolymer was prepared as follows: 25.16 g of diphenylmethane-4,4'-diisocyanate (MDI) and 126 ml of DMAc were added into a 250 ml two-neck flask and stirred to dissolve at room temperature. 5.44 g of 1,4-butanediol (BDO) was added into 27 ml of DMAc with thorough mixing. The mixture of 1,4-butanediol (BDO) and DMAc into the MDI solution with thorough mixing. Thereafter, the solution was heated to a temperature of between 60±5° C. for reaction for 3 hours to obtain a prepolymer. The weight-average molecular weight of the prepolymer measured by gel permeation chromatography (GPC) was about 4,581 dalton.

10.22 g of modified polyphenylene oxide (mPPO, weight-average molecular weight of 2,500) and 51.5 ml of DMAc were added into a 150 ml single-neck flask and shaken to dissolve at room temperature. 103 ml of the above mentioned mPPO solution was placed in an isobaric funnel and dripped slowly into the 60±5° C. prepolymer solution for about 30 minutes. After the addition of the mPPO solution was completed, the solution was stirred at 60±5° C. for 2.5 hours to obtain the PPU-NCO prepolymer. The weight-average molecular weight of the PPU-NCO prepolymer measured by gel permeation chromatography (GPC) was about 9,764 dalton.

Step 3. Brush Polymer

An amount of 1 g polyvinyl alcohol (PVA, weight-average molecular weight of 10,000) was added into 3 sample bottles each containing 6 mL of N,N-dimethylacetamide (DMAc) in 20 ml sample bottles, respectively, and the sample bottles were then placed in a drying oven at 65° C. for dissolution, and cooled to room temperature. Then, the obtained solution was respectively added 338 ml, 300 ml, and 263 ml of the above mentioned hydrophilic molecular branch prepolymer, $mPEG_{5000}$-NCO, and the mixture was heated to a temperature of between 60±5° C. for reaction for 3 hours to obtain the product, $PVA_{10,000}$-g-PEG5,000. Then, 25.6 ml, 51.1 ml, and 76.7 m of hydrophobic molecular branch prepolymer, $PPU_{9,764}$-NCO, were respectively added into the above mentioned $PVA_{10,000}$-g-$PEG_{5,000}$ product, and 0.01 g, 0.02 g, and 0.03 g of 1,4-diazabicyclo-(2,2,2) octane (DABCO) and 0.005 g, 0.01 g, and 0.015 g of $Sn(Oct)_2$ were respectively added with thorough mixing. Thereafter, the solution was heated to 65° C. for reaction for 16 hours to obtain $PVA_{10,000}$-g-($PEG_{5,000}$-co-$PPU_{9,764}$). The graft ratios of the hydrophilic PEG molecular branch were 70%, 80%, and 90% respectively, and that of the hydrophobic molecular branch (mPPU) were 30%, 20%, and 10% respectively.

The brush polymer was purified by a process as follows: the reacted product was dialysed in a dimethyl sulfoxide (DMSO) solution by MWCO: 25K dialysis membrane for 2 days, and finally dialysed in deionized water (DI water) by MWCO: 25K dialysis membrane for 2 day and then freeze dried.

EXAMPLE 19

Brush Polymer (1) (PVA-g-(Farnesol-co-$PPU_{4,923}$))

Step 1. Hydrophobic Molecular Branch Prepolymer (PPO-b-PU-NCO, PPU-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day in advance. The prepolymer was prepared as follows: 5.32 g of diphenylmethane-4,4'-diisocyanate (MDI) and 26.6 ml of DMAc were added into a 250 ml two-neck flask and stirred to dissolve at room temperature. 0.58 g of 1,4-butanediol (BDO) was added into 2.9 ml of DMAc with thorough mixing. The mixture of 1,4-butanediol (BDO) and DMAc were added into the MDI solution with thorough mixing. Thereafter, the solution was heated to a temperature of between 60±5° C. for reaction for 3 hours to obtain a prepolymer. The weight-average molecular weight of the prepolymer measured by gel permeation chromatography (GPC) was about 1,447 dalton.

10.22 g of modified polyphenylene oxide (mPPO, weight-average molecular weight of 2,500) and 51.5 ml of DMAc were added into a 150 ml single-neck flask and shaken to dissolve at room temperature. The mPPO solution was placed in an isobaric funnel and dripped slowly into the 60±5° C. prepolymer solution for about 30 minutes. After the addition of the mPPO solution was completed, the solution was stirred at 60±5° C. for 2.5 hours to obtain the PPU-NCO prepolymer. The weight-average molecular weight of the PPU-NCO prepolymer measured by gel permeation chromatography (GPC) was about 4,923 dalton.

Step 2. Brush Prepolymer (PVA-g-(Farnesol-co-PPU$_{4,923}$))

Before preparing the PVA-g-Farnesol prepolymer, N,N-dimethylacetamide (DMAc) solvent was dehydrated by a molecular sieve for one day in advance, and PVA was subjected to vacuum drying for 24 hours. 1 g of polyvinyl alcohol (PVA, weight-average molecular weight of 10,000) was added in to 2 ml of N,N-dimethylacetamide (DMAc) solvent in a 50 ml two-neck flask, and dissolved at a temperature of 60° C. in a drying oven. Then, 3.028 g of the anti-microbial molecular branch prepolymer (A) (Farnesol-HDI-NCO) of Example 7 was added into 63.6 ml of DMAc and stirred followed by added into the above mentioned PVA solution and mixed uniformly. Then, 0.016 g of 1,4-diazabicyclo-(2, 2,2) octane (DABCO) and 0.008 g of Sn(Oct)$_2$ were added, followed by being heated-up to 65° C. for reaction for 16 hours to obtain the prepolymer, PVA-g-Farnesol. PVA-g-Farnesol prepolymer was added into the above mentioned 13.5 ml of hydrophobic molecular branch prepolymer and mixed uniformly. A heating reaction was then carried out for 6 hours to heat up the mixture to 60° C. PVA-g-(Farnesol-co-PPU$_{4,923}$) was obtained after the reaction. The graft ratios of the hydrophilic Farnesol molecular branch were 30% and 60% respectively, and that of the hydrophobic molecular branch (PU) were 30% and 30% respectively.

EXAMPLE 20

Anti-Microbial Molecular Branch Prepolymer (D) (Farnesol-b-PEG$_{2,000}$-NCO))

Step 1. Hydrophobic Molecular Branch Prepolymer (PPO-b-PU-NCO, PPU-NCO)

N,N-dimethylacetamide (DMAc) solvent, 1,4-butanediol (BDO), and modified polyphenylene oxide (mPPO, weight-average molecular weight of 2,500) were dehydrated by a molecular sieve for one day. The prepolymer was prepared as follows: 4.86 g diphenylmethane-4,4'-diisocyanate (MDI) and 24.3 ml DMAc were added into a 250 ml two-neck flask and stirred to dissolve at room temperature. 0.34 g 1,4-butanediol (BDO) was added into 1.7 ml DMAc with thorough mixing. The mixture of 1,4-butanediol (BDO) and DMAc were added into the MDI solution with thorough mixing. Thereafter, the solution was heated to a temperature of between 60±5° C. for reaction for 3 hours to obtain a prepolymer. The weight-average molecular weight of the prepolymer measured by gel permeation chromatography (GPC) was about 2,254 dalton.

5.77 g modified polyphenylene oxide (mPPO, weight-average molecular weight of 2,500) and 28.83 ml DMAc were added into a 150 ml single-neck flask and shaken to dissolve at room temperature. The mPPO solution was placed in an isobaric funnel and dripped slowly into the 60±5° C. prepolymer solution for about 30 minutes. After the addition of the mPPO solution was completed, the solution was stirred at 60±5° C. for 2.5 hours to obtain the PPU-NCO prepolymer. The weight-average molecular weight of the PPU-NCO prepolymer measured by gel permeation chromatography (GPC) was about 10,171 dalton.

Step 2. Brush Prepolymer (PVA-g-(Farnesol-b-PEG-co-PPU$_{10,171}$))

Before preparing the PVA-g-(Farnesol-b-PEG$_{200}$) prepolymer, N,N-dimethylacetamide (DMAc) solvent was dehydrated by a molecular sieve for one day in advance, and PVA was subjected to vacuum drying for 24 hours. The prepolymer was prepared as follows: 0.027 g polyvinyl alcohol (PVA, weight-average molecular weight of 10,000) was added in to 0.1 ml N,N-dimethylacetamide (DMAc) solvent in a 50 ml two-neck flask, and dissolved at a temperature of 60° C. in a drying oven. Then, 0.814 g the anti-microbial molecular branch prepolymer of Example 8 was added into 49.73 ml DMAc and stirred followed by added into the above mentioned PVA solution and mixed uniformly. Then, 0.0034 g 1,4-diazabicyclo-(2,2,2) octane (DABCO) and 0.0017 g Sn(Oct)$_2$ were added, followed by being heated-up to a temperature of between 65±5° C. for reaction for 16 hours to obtain the prepolymer, PVA-g-(Farnesol-b-PEG$_{200}$).

Then, ⅓ of the prepolymer, PVA-g-(Farnesol-b-PEG$_{200}$), was added into 1.8 ml of the above mentioned hydrophobic molecular branch prepolymer, PPU-NCO, and mixed uniformly followed by being heated-up to a temperature of between 60±5° C. for reaction for 6 hours to obtain the polymer, PVA-g-(Farnesol-b-PEG$_{2,000}$-co-PPU$_{10,171}$), wherein the graft ratios of the hydrophilic molecular branch (Farnesol-b-PEG$_{2,000}$) were 50% and the hydrophobic molecular branch (PPU) were 30%.

Before preparing the PVA-g-(Farnesol-b-PEG$_{10,000}$) prepolymer, N,N-dimethylacetamide (DMAc) solvent was dehydrated by a molecular sieve for one day in advance, and PVA was subjected to vacuum drying for 24 hours. The prepolymer was prepared as follows: 0.08 g polyvinyl alcohol (PVA, weight-average molecular weight of 10,000) was added in to 0.8 ml N,N-dimethylacetamide (DMAc) solvent in a 50 ml two-neck flask, and dissolved at a temperature of 60° C. in a drying oven. Then, 9.3 g the anti-microbial molecular branch prepolymer of Example 8 was added into 102.2 ml DMAc and stirred followed by added into the above mentioned PVA solution. Then, 0.0038 g 1,4-diazabicyclo-(2,2,2) octane (DABCO) and 0.0019 g Sn(Oct)$_2$ were added, followed by being heated-up to a temperature of between 65±5° C. for reaction for 16 hours to obtain the prepolymer, PVA-g-(Farnesol-b-PEG$_{10,000}$).

Then, ⅓ of the amount of the prepolymer, PVA-g-(Farnesol-b-PEG$_{10,000}$), was added into 2.52 ml of the above mentioned hydrophobic molecular branch prepolymer, PPU-NCO, and mixed uniformly followed by being heated-up to a temperature of between 60±5° C. for reaction for 6 hours to obtain the polymer, PVA-g-(Farnesol-b-PEG$_{10,000}$-co-PPU), wherein the graft ratios of the hydrophilic molecular branch (Farnesol-b-PEG$_{10,000}$) were 50% and that of the hydrophobic molecular branch (PPU) were 30%.

EXAMPLE 21

Hydrophobic Substrate Dipped in Brush Polymer Resolution

The dipping procedure of a hydrophobic substrate in a brush polymer solution was as follows. The brush polymers of Examples 11-20 were agitated in solutions in accordance with the compositions and ratios listed in Table 1 for dissolution, and the resulting brush polymer solution was placed in a glass container. A hydrophobic film substrate (thermoplastic polyurethane film, TPU film) was dipped into the brush polymer solution for 20 seconds, and placed in a dry oven at a temperature of between 65±5° C. for removal of solvent for 2 hours.

TABLE 1

| Sample No. | Example | Brush polymer composition | Brush polymer in solvent (%) | acetone | butanone | water | DMF | DMSO |
|---|---|---|---|---|---|---|---|---|
| #1 | Example (11) | PVA-g-(PEG-co-mC$_8$PU) | 5:95 | — | 25 | 75 | — | — |
| #2 | | PEG graft ratio = 60% | | — | 50 | 50 | — | — |
| #3 | | mC$_8$PU graft ratio = 30% | | — | 75 | 25 | — | — |
| #4 | Example (12) | PVA-g-(PEG-co-mC$_8$PU) | 5:95 | — | 25 | 75 | — | — |
| #5 | | PEG graft ratio = 60% | | — | 50 | 50 | — | — |
| #6 | | mC$_8$PU graft ratio = 10% | | — | 75 | 25 | — | — |
| #7 | Example (11) | PVA-g-(PEG-co-mC$_8$PU) | 5:95 | — | 70 | — | 30 | — |
| #8 | | PEG graft ratio = 60% | | — | 80 | — | 20 | — |
| #9 | | mC$_8$PU graft ratio = 30% | | — | 90 | — | 10 | — |
| #10 | Example (12) | PVA-g-(PEG-co-mC$_8$PU) | 5:95 | — | 70 | — | 30 | — |
| #11 | | PEG graft ratio = 60% | | — | 80 | — | 20 | — |
| #12 | | mC$_8$PU graft ratio = 10% | | — | 90 | — | 10 | — |
| #13 | Example (11) | PVA-g-(PEG-co-mC$_8$PU) | 5:95 | 80 | — | — | 20 | — |
| #14 | | PEG graft ratio = 60% | | — | — | 80 | 20 | — |
| #15 | | mC$_8$PU graft ratio = 30% | | 40 | — | 40 | 20 | — |
| #16 | Example (12) | PVA-g-(PEG-co-mC$_8$PU) | 5:95 | 80 | — | — | 20 | — |
| #17 | | PEG graft ratio = 60% | | — | — | 80 | 20 | — |
| #18 | | mC$_8$PU graft ratio = 10% | | 40 | — | 40 | 20 | — |
| #19 | Example (13) | PVA-g-(PEG-co-mC$_8$PU) | 5:95 | 80 | — | — | 20 | — |
| #20 | | PEG graft ratio = 30% | | — | — | 80 | 20 | — |
| #21 | | mC$_8$PU graft ratio = 10% | | 40 | — | 40 | 20 | — |
| #22 | Example (14) | PVA-g-(PEG-co-mC$_8$PU) | 5:95 | 80 | — | — | 20 | — |
| #23 | | PEG graft ratio = 60% | | — | — | 80 | 20 | — |
| #24 | | mC$_8$PU graft ratio = 10% | | 40 | — | 40 | 20 | — |
| #25 | Example (15) | PVA-g-(PEG-co-mC$_8$PU) | 5:95 | 80 | — | — | 20 | — |
| #26 | | PEG graft ratio = 90% | | — | — | 80 | 20 | — |
| #27 | | mC$_8$PU graft ratio = 10% | | 40 | — | 40 | 20 | — |
| #28 | Example (16) | PVA-g-(PEG-co-PPO) PEG graft ratio = 60% PPO graft ratio = 10% | 5:95 | 80 | — | — | 20 | — |
| #29 | Example (17) | PVA-g-(PEG-co-PPU) | 5:95 | 60 | — | — | 20 | 20 |
| #30 | | PEG graft ratio = 70% | | 80 | — | 20 | — | — |
| #31 | | PPU graft ratio = 30% | | 20 | — | — | 80 | — |
| #32 | Example (18) | PVA-g-(PEG-co-PPU) | 5:95 | 60 | — | — | 20 | 20 |
| #33 | | PEG graft ratio = 70% | | 80 | — | 20 | — | — |
| #34 | | PPU graft ratio = 30% | | 20 | — | — | 80 | — |
| #35 | Example (17) | PVA-g-(PEG-co-PPU) | 1:99 | 80 | — | — | 20 | — |
| #36 | | PEG graft ratio = 70% PPU graft ratio = 30% | | 95 | — | — | 5 | — |
| #37 | Example (19) | PVA-g-(Farnesol-co-PPU) Farnesol graft ratio = 60% PPU graft ratio = 30% | 1:99 | 80 | — | — | 20 | — |
| #38 | Example (20) | PVA-g-(Farnesol-b-PEG-co-PPU) Farnesol-b-PEG graft ratio = 50% PPU graft ratio = 30% | 1:99 | 80 | — | — | 20 | — |

EXAMPLE 22

Surface Contact Angle Test (A)

In the surface contact angle test, the un-coated thermoplastic polyurethane film (un-coated TPU film, aromatic type, hardness: shore 95 A) and the film coated with the brush polymer solution of Example 20 were tested. The test samples had a thickness of 0.3 mm and a surface area of 5 cm×2 cm (length×width). Distilled de-ionized water (DD water) was used as the solution for the surface contact angle test. After a drop of the DD water contacted with a sample for 30 seconds, the contact angle of water drop was measured, and the results are illustrated in Table 2 (n=3).

TABLE 2

Material composition, solvent composition, and water surface contact angle

| Sample No. | Example | Brush polymer composition | acetone | butanone | water | DMF | DMSO | water surface contact angle (°) |
|---|---|---|---|---|---|---|---|---|
| C#1 | Control | Un-coated TPU film (hardness = shore 95A) | — | — | — | — | — | 73.5 ± 0.4 |
| #1 | Example (11) | PVA-g-(PEG-co-mC$_8$PU) | — | 25 | 75 | — | — | 73.3 ± 5.4 |
| #2 | | PEG graft ratio = 60% | — | 50 | 50 | — | — | 72.3 ± 0.7 |
| #3 | | mC$_8$PU graft ratio = 30% | — | 75 | 25 | — | — | 81.3 ± 0.7 |
| #4 | Example (12) | PVA-g-(PEG-co-mC$_8$PU) | — | 25 | 75 | — | — | 37.0 ± 3.9 |
| #5 | | PEG graft ratio = 60% | — | 50 | 50 | — | — | 44.3 ± 2.5 |
| #6 | | mC$_8$PU graft ratio = 10% | — | 75 | 25 | — | — | 31.4 ± 3.9 |
| #7 | Example | PVA-g-(PEG-co-mC$_8$PU) | — | 70 | — | 30 | — | 53.7 ± 3.3 |

TABLE 2-continued

Material composition, solvent composition, and water surface contact angle

| Sample No. | Example | Material Brush polymer composition | acetone | butanone | water | DMF | DMSO | water surface contact angle (°) |
|---|---|---|---|---|---|---|---|---|
| #8 | (11) | PEG graft ratio = 60% | — | 80 | — | 20 | — | 37.5 ± 7.0 |
| #9 | | mC$_8$PU graft ratio = 30% | — | 90 | — | 10 | — | 38.6 ± 5.6 |
| #10 | Example | PVA-g-(PEG-co-mC$_8$PU) | — | 70 | — | 30 | — | 72.2 ± 1.6 |
| #11 | (12) | PEG graft ratio = 60% | — | 80 | — | 20 | — | 63.6 ± 3.7 |
| #12 | | mC$_8$PU graft ratio = 10% | — | 90 | — | 10 | — | 82.8 ± 8.3 |
| #13 | Example | PVA-g-(PEG-co-mC$_8$PU) | 80 | — | — | 20 | — | 49.4 ± 3.3 |
| #14 | (11) | PEG graft ratio = 60% | — | — | 80 | 20 | — | 87.2 ± 4.8 |
| #15 | | mC$_8$PU graft ratio = 30% | 40 | — | 40 | 20 | — | 95.2 ± 1.9 |
| #16 | Example | PVA-g-(PEG-co-mC$_8$PU) | 80 | — | — | 20 | — | 36.9 ± 4.6 |
| #17 | (12) | PEG graft ratio = 60% | — | — | 80 | 20 | — | 57.0 ± 4.4 |
| #18 | | mC$_8$PU graft ratio = 10% | 40 | — | 40 | 20 | — | 44.2 ± 3.8 |
| #19 | Example | PVA-g-(PEG-co-mC$_8$PU) | 80 | — | — | 20 | — | 60.6 ± 1.4 |
| #20 | (13) | PEG graft ratio = 30% | — | — | 80 | 20 | — | 53.0 ± 6.1 |
| #21 | | mC$_8$PU graft ratio = 10% | 40 | — | 40 | 20 | — | 59.3 ± 2.1 |
| #22 | Example | PVA-g-(PEG-co-mC$_8$PU) | 80 | — | — | 20 | — | 36.9 ± 4.6 |
| #23 | (14) | PEG graft ratio = 60% | — | — | 80 | 20 | — | 54.7 ± 5.4 |
| #24 | | mC$_8$PU graft ratio = 10% | 40 | — | 40 | 20 | — | 44.1 ± 5.1 |
| #25 | Example | PVA-g-(PEG-co-mC$_8$PU) | 80 | — | — | 20 | — | 31.5 ± 2.6 |
| #26 | (15) | PEG graft ratio = 90% | — | — | 80 | 20 | — | 41.7 ± 3.8 |
| #27 | | mC$_8$PU graft ratio = 10% | 40 | — | 40 | 20 | — | 27.3 ± 6.2 |
| #28 | Example (16) | PVA-g-(PEG-co-PPO) PEG graft ratio = 60% PPO graft ratio = 10% | 80 | — | — | 20 | — | 47.6 ± 3.2 |
| #29 | Example | PVA-g-(PEG-co-PPU) | 60 | — | — | 20 | 20 | 73.7 ± 2.6 |
| #30 | (17) | PEG graft ratio = 70% | 80 | — | 20 | — | — | 48.5 ± 5.2 |
| #31 | | PPU graft ratio = 30% | 80 | — | — | 20 | — | 66.3 ± 1.4 |
| #32 | Example | PVA-g-(PEG-co-PPU) | 60 | — | — | 20 | 20 | 45.7 ± 1.2 |
| #33 | (18) | PEG graft ratio = 70% | 80 | — | 20 | — | — | 45.9 ± 3.6 |
| #34 | | PPU graft ratio = 30% | 80 | — | — | 20 | — | 47.8 ± 2.6 |
| #35 | Example | PVA-g-(PEG-co-PPU) | 80 | — | — | 20 | — | — |
| #36 | (17) | PEG graft ratio = 70% PPU graft ratio = 30% | 95 | — | — | 5 | — | — |
| #37 | Example (19) | PVA-g-(Farnesol-co-PPU) Farnesol graft ratio = 60% PPU graft ratio = 30% | 80 | — | — | 20 | — | — |
| #38 | Example (20) | PVA-g-(Farnesol-b-PEG-co-PPU) Farnesol-b-PEG graft ratio = 50% PPU graft ratio = 30% | 80 | — | — | 20 | — | — |

EXAMPLE 23

Surface Contact Angle Test (B)

Figure 4:
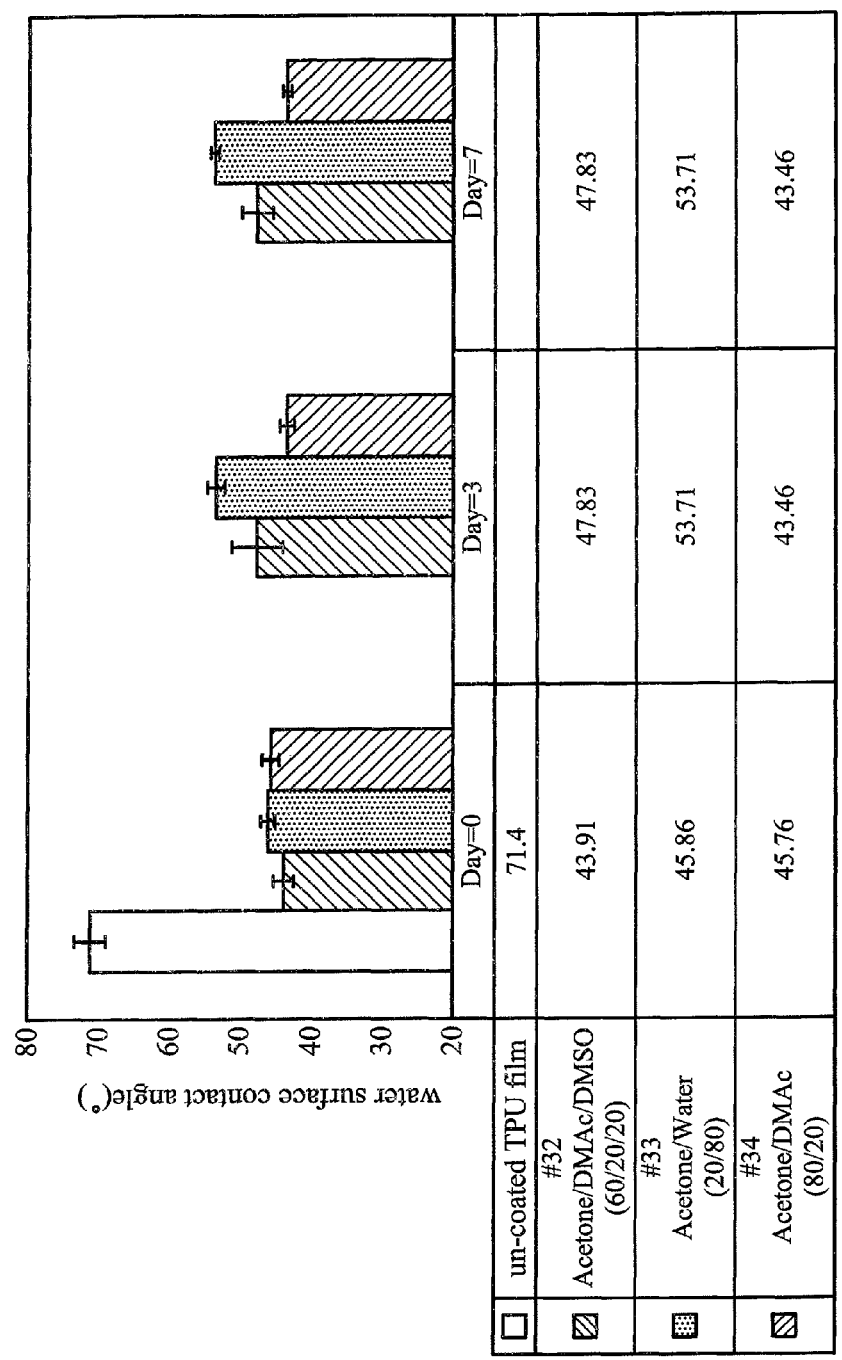
FIG. 4 illustrates the adhesion stability between a hydrophobic molecular branch and a matrix according to embodiments of the present disclosure.

In the surface contact angle test, the un-coated thermoplastic polyurethane film (un-coated TPU film, aromatic type, hardness=shore 95 A) and the film coated with the brush polymer solution of Example 20 were tested. Before testing, the samples were agitated, washed with DD water for 30 minutes, dipped in phosphate buffer saline (PBS buffer) at a temperature of 37° C. for 3 days and 7 days, and then washed with DD water and air dried at room temperature for testing. The test samples had a thickness of 0.3 mm and a surface area of 5 cm×2 cm (length×width). Distilled de-ionized water (DD water) was used as the solution for the surface contact angle test. After a drop of the DD water contacted with a sample for 30 seconds, the contact angle of water drop was measured, and the results are illustrated in FIG. 4 (n=3).

EXAMPLE 24

Protein Adsorption Test

The thermoplastic polyurethane films (aromatic type, hardness: shore 85 A and 65 D) were coated with the brush polymer solution. Before the fibrinogen adhesion test, the standard solution and the standard curve were prepared as follows: 2 mg/ml fibrinogen solution was diluted to 50, 100, 250, 500, 1000, and 2000 μg/ml of fibrinogen solution with DD water. The standard solution was diluted to 5, 10, 25, 50, 100, and 200 μg/ml of fibrinogen solution with 1% sodium dodecyl sulfate (1% SDS), and then absorption of each solution was obtained with an ELISA reader for plotting the standard curve.

Next, the samples were cut into a size of 2 cm×1.5 cm and put in a 15 ml centrifuge tube followed by adding 15 ml (4.5 mg/ml) of fibrinogen solution respectively, and then placed in an incubator at a temperature of 37° C. for 24 hours of adhesion. After 24 hours of adhesion, the fibrinogen solution was removed, and the samples were washed by dipping in PBS buffer twice. Then, each sample was placed in a microcentrifuge tube containing 5 ml 1.0% SDS and ultrasonicated for 20 minutes, and the SDS solution extracted fibrinogen was collected. Absorption of the SDS solution at 750 nm was measured with an ELISA reader, and compared with the standard curve plotted by fibrinogen solutions with different concentrations, to obtain the fibrinogen concentration of each sample. The results are illustrated in Table 3 (n=3).

TABLE 3

Absorption of Fibrinogen

| Sample # | | Absorption of Fibrinogen ($\mu g/cm^2$) |
|---|---|---|
| Control (A) TPU film (hardness = shore 85A) | Un-coated | 11.4 ± 4.7 |
| Example (13) #19 | PVA-g-(PEG-co-mC$_8$PU) PEG graft ratio = 30% mC$_8$PU graft ratio = 10% | 3.3 ± 2.9 |
| Example (14) #22 | PVA-g-(PEG-co-mC$_8$PU) PEG graft ratio = 60% mC$_8$PU graft ratio = 10% | 5.2 ± 1.5 |
| Example (15) #25 | PVA-g-(PEG-co-mC$_8$PU) PEG graft ratio = 90% mC$_8$PU graft ratio = 10% | 6.4 ± 1.6 |
| Control (B) TPU film (hardness = shore 65D) | Un-coated | 11.8 ± 4.0 |
| Example (13) #19 | PVA-g-(PEG-co-mC$_8$PU) PEG graft ratio = 30% mC$_8$PU graft ratio = 10% | 5.4 ± 1.3 |
| Example (14) #22 | PVA-g-(PEG-co-mC$_8$PU) PEG graft ratio = 60% mC$_8$PU graft ratio = 10% | 7.4 ± 5.7 |
| Example (15) #25 | PVA-g-(PEG-co-mC$_8$PU) PEG graft ratio = 90% mC$_8$PU graft ratio = 10% | 1.5 ± 1.0 |
| Control (C) TPU film (hardness = shore 85A) | 5% Gelatin coated | 151.3 ± 30.3 |
| Control (D) TPU film (hardness = shore 85A) | 2.5% Collagen coated | 727.7 ± 52.6 |

EXAMPLE 25

In-Vitro Cell Adhesion Assay

The thermoplastic polyurethane films (aromatic type, hardness: shore 85 A and 65 D) were coated with the brush polymer solution. Before the cell adhesion test in vitro, each sample was placed in a 24-well plate and fixed by a glass tube and a nontoxic ring. Mice fibroblast L929 cells and human dermal fibroblast CCD-966SK cells solutions were respectively put in each well with a concentration of $1 \times 10^5$ cell/well and cultured in an incubator at a temperature of 37° C. for 24 and 48 hours, followed by dipping in PBS for several times to wash each sample. Then, the adhered cells were fixed with 4% paraformaldehyde, and the samples were washed with PBS after removing paraformaldehyde. Next, fluorescent dye (DAPI, Phalloidine) was added to the samples, and the cell profile was observed through a fluorescence microscope, and the number of the cells adhered on each sample was counted. The results of the cell adhesion test in vitro are illustrated in Table 4 and Table 5.

TABLE 4

Cell adhesion of L929 cell in vitro

| Sample No./coating material | | L929 cell adhesion (cell/mm$^2$) Cultured for 24 hours | L929 cell adhesion (cell/mm$^2$) Cultured for 48 hours |
|---|---|---|---|
| Control (A) TPU film (hardness = shore 85A) | Un-coated | 198 | 915 |
| Example (13) #19 | PVA-g-(PEG-co-mC$_8$PU) PEG graft ratio = 30% mC$_8$PU graft ratio = 10% | 0 | 29 |
| Example (14) #22 | PVA-g-(PEG-co-mC$_8$PU) PEG graft ratio = 60% mC$_8$PU graft ratio = 10% | 0 | 23 |
| Example (15) #25 | PVA-g-(PEG-co-mC8PU) PEG graft ratio = 90% mC$_8$PU graft ratio = 10% | 0 | 26 |
| Control (B) TPU film (hardness = shore 65D) | Un-coated | 371 | 491 |
| Example (13) #19 | PVA-g-(PEG-co-mC8PU) PEG graft ratio = 30% mC$_8$PU graft ratio = 10% | 0 | 69 |
| Example (14) #22 | PVA-g-(PEG-co-mC$_8$PU) PEG graft ratio = 60% mC$_8$PU graft ratio = 10% | 0 | 31 |
| Example (15) #25 | PVA-g-(PEG-co-mC$_8$PU) PEG graft ratio = 90% mC$_8$PU graft ratio = 10% | 0 | 17 |

TABLE 5

Cell adhesion of CCD-966SK cell in vitro

| Sample No./coating material composition | | CCD-966SK cell adhesion (cell/mm$^2$) Cultured for 48 hours |
|---|---|---|
| Control (A) TPU film (hardness = shore 85A) | Un-coated | 417 |
| Example (13) #19 | PVA-g-(PEG-co-mC$_8$PU) PEG graft ratio = 30% mC$_8$PU graft ratio = 10% | 99 |
| Example (14) #22 | PVA-g-(PEG-co-mC$_8$PU) PEG graft ratio = 60% mC$_8$PU graft ratio = 10% | 105 |
| Example (15) #25 | PVA-g-(PEG-co-mC$_8$PU) PEG graft ratio = 90% mC$_8$PU graft ratio = 10% | 30 |
| Control (B) TPU film (hardness = shore 65D) | Un-coated | 463 |
| Example (13) #19 | PVA-g-(PEG-co-mC$_8$PU) PEG graft ratio = 30% mC$_8$PU graft ratio = 10% | 101 |
| Example (14) #22 | PVA-g-(PEG-co-mC$_8$PU) PEG graft ratio = 60% mC$_8$PU graft ratio = 10% | 63 |
| Example (15) #25 | PVA-g-(PEG-co-mC$_8$PU) PEG graft ratio = 90% mC$_8$PU graft ratio = 10% | 24 |

EXAMPLE 26

In Vivo Anti-Adhesion Test

Figure 5:
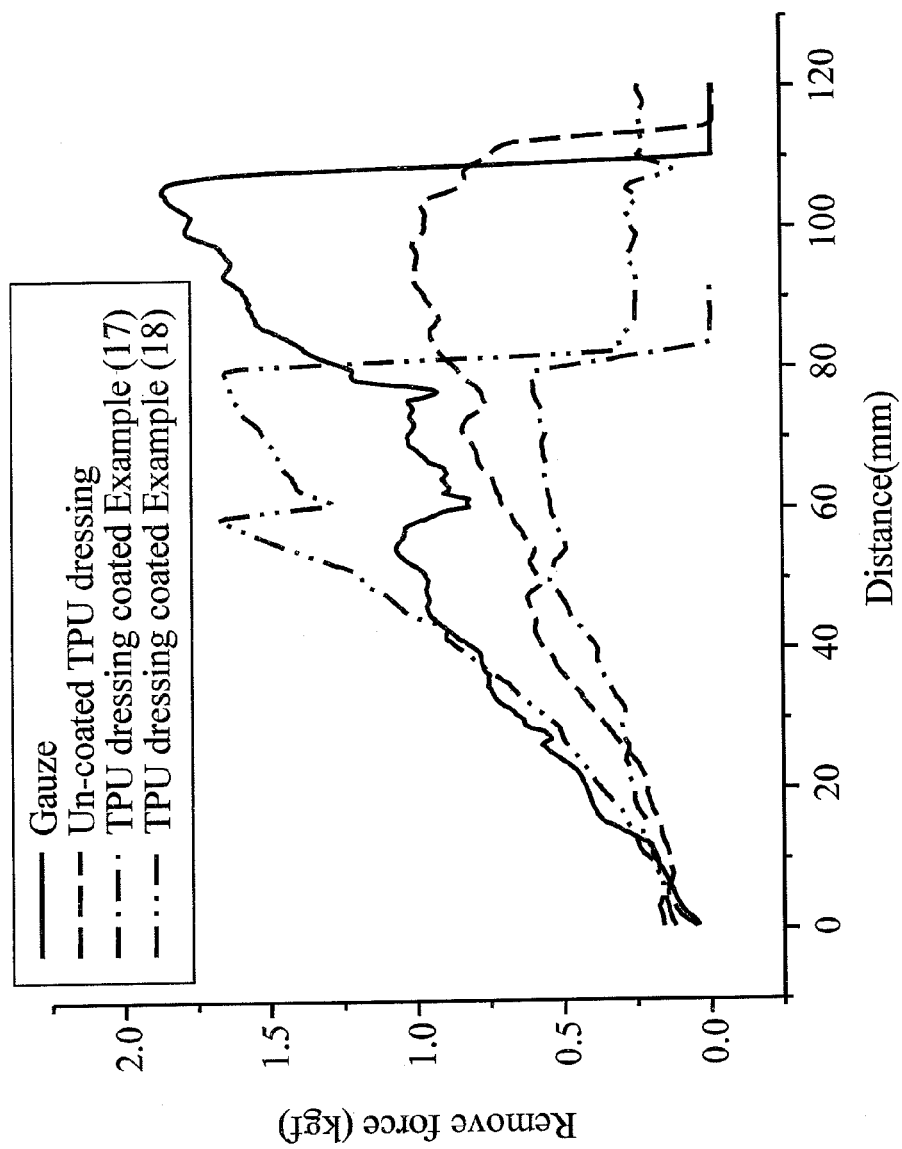
FIG. 5 illustrates the result of the anti-adhesion test (in vivo) by showing the removal force and the wound distance of each sample according to embodiments of the present disclosure.

Anti-adhesion test was performed in vivo with Wistar rats (National Experimental Animals Production Center, Taiwan) by wound adhesion test. The area of the opened wound on the back of rat's body was 6 cm×5 cm (full-thickness wound). On the 3rd day after the wound was opened, each sample (gauze; un-coated TPU dressing; TPU dressing coated Example (17); TPU dressing coated Example (18)) was fixed onto the wound, and the surface was covered with a breathable water-proof dressing (transparent Tegaderm™, 3M HealthCare, Borken, Germany). On the 8th day after the wound was opened, the maximum strength required for peeling off the dressing and the total wound area were recorded by a tension tester with a steady tension speed of 4 mm/s. The result is illustrated in FIG. 5 and Table 6 which show the remove force and the wound distance of each sample.

TABLE 6 anti-adhesion test (in vivo)

|  | Gauze | Un-coated TPU dressing | TPU dressing coated Example (17) | TPU dressing coated Example (18) |
|---|---|---|---|---|
| Remove force (total area) | 102.9 | 67.5 | 32.1 | 62.7 |
| Remove force Peak Force (kgf) | 1.87 | 1.01 | 0.61 | 1.68 |
| peak distance (mm) | 106.0 | 97.6 | 79.2 | 58.8 |
| Total distance (mm) | 110.4 | 114.8 | 83.6 | 87.2 |

EXAMPLE 27

Anti-Microbial Effect

In the anti-microbial effect evaluation, the thermoplastic polyurethane films (aromatic type, hardness=shore 95 A) were coated with the brush polymer solution. The microbial used here was Pseudomonas aeruginosa. Before the anti-microbial effect evaluation, the samples were illuminated by UV for 20 minutes for sterilization. The qualitative description of each sample was based on the relative bacterial growth level between control (Un-coated TPU film) and the films coated with the brush polymer solutions. The results are illustrated in Table 6.

TABLE 7

Anti-microbial effect of sample

| Sample No./coating material composition |  | Anti-microbial effect "−" none "+" light "++" medium "+++" high |
|---|---|---|
| Control (A) TPU film (hardness = shore 95A) | Un-coated | − |
| Example (19) #37 | PVA-g-(Farnesol-co-PPU) Farnesol graft ratio = 60% PPU graft ratio = 30% | ++ |
| Example (20) #38 | PVA-g-(Farnesol-b-PEG-co-PPU) Farnesol-b-PEG graft ratio = 50% PPU graft ratio = 30% | ++ |

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

What is claimed is:

1. A brush polymer, comprising:
   (a) a linear polymer main chain; and
   (b) brush structural side chains, comprising:
      (b1) a hydrophobic molecular branch, wherein the hydrophobic molecular branch comprises polyurethane, and
      (b2) a hydrophilic molecular branch and an anti-biofilm or an anti-microbial molecular branch, wherein the anti-biofilm or the anti-microbial molecular branch comprises farnesol, xylitol, lactoferrin, ethylene diamine tetraacetic acid (EDTA), gallium, PNAG-degrading enzyme, RNA-III inhibiting peptide, furanone C30, silver, iodine, zinc, copper, an antibiotic, medicine or combinations thereof,
   wherein the linear polymer main chain is conjugated to the brush structural side chains by covalent bonds formed between a hydroxyl group and a reactive functional group, wherein the reactive functional group comprises: isocyanate, carboxyl, or epoxy, wherein the anti-biofilm or the anti-microbial molecular branch conjugates onto the linear polymer main chain by a covalent bond.

2. The brush polymer of claim 1, wherein the linear polymer main chain comprises: polyvinyl alcohol (PVA), polyvinyl acetate (PVAc), poly(vinyl alcohol-co-vinyl acetate), poly(ethylene vinyl-co-alcohol) (EVOH), polysaccharide, or combinations thereof.

3. The brush polymer of claim 1, wherein the hydrophobic molecular branch comprises: aliphatic polyurethane, aromatic polyurethane, or combinations thereof.

4. The brush polymer of claim 1, wherein the hydrophobic molecular branch has a weight-average molecular weight of about 500 to 50,000 dalton.

5. The brush polymer of claim 1, wherein the hydrophilic molecular branch comprises: polyethylene glycol, (PEG), polyethylene oxide (PEO), polyvinylpyrrolidone (PVP), polyacrylic acid (PAA), polymethacrylic acid (PMA), or combinations thereof.

6. The brush polymer of claim 5, wherein the hydrophilic molecular branch has a weight-average molecular weight of about 500 to 100,000 dalton.

7. The brush polymer of claim 1, wherein the hydrophilic molecular branch comprises: polyethylene glycol, (PEG), polyethylene oxide (PEO), polyvinylpyrrolidone (PVP), or combinations thereof.

8. The brush polymer of claim 1, wherein the linear polymer main chain is conjugated to the brush structural side chains by a covalent bond comprising a urethane linkage.

9. A medical device, wherein the medical device has the brush polymer of claim 1 adhered to its surface and/or blended therein.

10. The medical device of claim 9, wherein the medical device comprises a polymer comprising: thermoplastic polyurethane (TPU), polyurethane (PU), polyvinyl alcohol, (PVA), polyethylene (PE), polypropylene (PP), polyvinyl chloride (PVC), polystyrene, polyvinyl acetate (PVAc), poly (vinyl alcohol-co-vinyl acetate), poly(ethylene vinyl-co-alcohol) (EVOH), polysulfone, poly ether sulfone, or combinations thereof.

11. The medical device of claim 9, wherein the medical device is a wound dressing, a catheter, a vascular access device, a hemodialyzer, a stent, a biliary stent, or an implantable device.

12. A method for modifying a medical device, comprising:
providing a brush polymer of claim 1;
dissolving the brush polymer in a solution; and
coating or dipping a medical device with the solution containing the brush polymer followed by a drying process, such that the brush polymer is attached to a surface of the medical device.

13. The method for modifying a medical device of claim 12, wherein the solution comprises: N,N-dimethylformamide (DMF), N,N-dimethylacetamide (DMAc), dimethyl sulfoxid (DMSO), tetrahydrofuran (THF), alcohols, ketones, water, or combinations thereof.

14. The method for modifying a medical device of claim 12, wherein the solution comprises: (a) butanone and water, (b) acetone and N,N-dimethylacetamide (DMAc), (c) acetone, water, and N,N-dimethylacetamide (DMAc), or (d) acetone, N,N-dimethylacetamide (DMAc), and dimethyl sulfoxid (DMSO).

15. The method for modifying a medical device of claim 12, wherein the drying process is performed by hot air or under vacuum at a temperature of room temperature to 200° C.

16. The method for modifying a medical device of claim 12, wherein the medical device comprises a polymer comprising: thermoplastic polyurethane (TPU), polyurethane (PU), polyvinyl alcohol (PVA), polyethylene (PE), polypropylene (PP), polyvinyl chloride (PVC), polystyrene, polyvinyl acetate (PVAc), poly(vinyl alcohol-co-vinyl acetate, poly(ethylene vinyl-co-alcohol) (EVOH), polysulfone, poly ether sulfone, or combinations thereof.

17. The method for modifying a medical device of claim 12, wherein the medical device comprises: a wound dressing, a catheter, a vascular access device, a hemodialyzer, a stent, a biliary stent, or an implantable device.

\* \* \* \* \*